United States Patent
Nakanishi et al.

(10) Patent No.: US 9,739,722 B2
(45) Date of Patent: Aug. 22, 2017

(54) REFLECTIVE MASK BLANK FOR EUV LITHOGRAPHY, AND PROCESS FOR ITS INSPECTION AND PROCESS FOR ITS PRODUCTION

(71) Applicant: Asahi Glass Company, Limited, Chiyoda-ku (JP)

(72) Inventors: Hiroshi Nakanishi, Chiyoda-ku (JP); Junichi Kageyama, Chiyoda-ku (JP); Yoshiaki Ikuta, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 158 days.

(21) Appl. No.: 14/878,181

(22) Filed: Oct. 8, 2015

(65) Prior Publication Data
US 2016/0109384 A1   Apr. 21, 2016

(30) Foreign Application Priority Data
Oct. 20, 2014  (JP) ................................ 2014-213394

(51) Int. Cl.
*G03F 1/22*   (2012.01)
*G03F 1/24*   (2012.01)
*G03F 1/72*   (2012.01)
*G01N 21/956*   (2006.01)
(Continued)

(52) U.S. Cl.
CPC ....... *G01N 21/956* (2013.01); *G01N 21/8851* (2013.01); *G03F 1/24* (2013.01); *G03F 1/84* (2013.01); *G01N 2021/95676* (2013.01)

(58) Field of Classification Search
None
See application file for complete search history.

(56) References Cited

U.S. PATENT DOCUMENTS

2013/0017475 A1* 1/2013 Terasawa ........... G01N 21/8806
430/5

FOREIGN PATENT DOCUMENTS

JP   2013-80810   5/2013

OTHER PUBLICATIONS

Takeshi Yamane et al. "Defect detection sensitivity improvement of actinic blank inspection", 2011 EUVL Symposium, EVUL Infrastructure Development Center, Inc. 2011, 21 pages.
(Continued)

*Primary Examiner* — Stephen Rosasco
(74) *Attorney, Agent, or Firm* — Oblon, McClelland, Maier & Neustadt, L.L.P.

(57) ABSTRACT

A process for inspecting an EUV mask blank capable of distinguishing phase defects and amplitude defects and capable of detecting small amplitude defects, a process for producing an EUV mask blank using the inspection process, and an EUV mask blank obtainable by such a process. A process for inspecting a reflective mask blank for EUV lithography having a multilayer reflective film and an absorber layer. The process includes a first step of detecting in-plane defects in the multilayer reflective film by applying EUV light to the surface of the multilayer reflective film, a second step of detecting in-plane defects from the absorber layer by applying light having a wavelength of from 150 to 600 nm to the surface of the absorber layer, and a step of distinguishing phase defects and amplitude defects in the reflective mask blank by comparison between the first and second in-plane defect data.

12 Claims, 2 Drawing Sheets

(51) Int. Cl.
    *G03F 1/84*    (2012.01)
    *G01N 21/88*   (2006.01)

(56) References Cited

OTHER PUBLICATIONS

Tsuneo Terasawa et al. "High Speed Actinic EUV Mask Blank Inspection with Dark-Field Imaging", Proceedings of SPIE vol. 5446, 2004, 5 pages.
Andy Ma et al. "Improvement of EUVL Mask Blank Defect Inspection Capability at Intel", Proc. SPIE, 7379, 2009, 24 pages.
Sungmin Huh et al. "Printability and Inspectability of Defects on the EUV Mask for sub32nm Half Pitch HVM Application", Proc. SPIE, vol. 7379, 2011, 37 pages.

* cited by examiner

REFLECTIVE MASK BLANK FOR EUV LITHOGRAPHY, AND PROCESS FOR ITS INSPECTION AND PROCESS FOR ITS PRODUCTION

TECHNICAL FIELD

The present invention relates to a process for inspecting a reflective mask blank for EUV (extreme ultraviolet) lithography (hereinafter referred to as "EUV mask blank" in this specification) to be used for the production of semiconductors, etc.

Further, the present invention relates to a process for producing an EUV mask blank using the process for inspecting an EUV mask blank of the present invention.

Still further, the present invention relates to an EUV mask blank obtained by the production process of the present invention.

BACKGROUND ART

Heretofore, in the semiconductor industry, a photolithography method employing visible light or ultraviolet light has been used as a technique to transfer a fine pattern required to form an integrated circuit with a fine pattern on a substrate such as a silicon wafer. A photolithography method is a means to form an integrated circuit pattern formed on a photomask, on a resist on a wafer by reduced projection by means of a projection optic system of an exposure machine. Along with miniaturization of patterns of semiconductor devices, as a source light of an exposure machine used at the time when an integrated circuit pattern on a photomask is transferred to a resist on a wafer, a shorter wavelength EUV light is prospective, rather than ArF excimer laser having a wavelength of 193 nm. EUV light is meant for a light ray having a wavelength within a soft X-ray region or within a vacuum ultraviolet region, specifically for a light ray having a wavelength of from 5 to 20 nm, particularly 13.5 nm±0.3 nm.

EUV light is likely to be absorbed by all kinds of substances, and the refractive index of substances at such a wavelength is close to 1, whereby it is not possible to use a conventional refractive system like photolithography employing visible light or ultraviolet light. Therefore, in EUV light lithography, a reflective system i.e. a combination of a reflective photomask and a mirror, is employed.

A mask blank is a stacked member before patterning, to be employed for the production of a photomask. In the case of an EUV mask blank, it has a structure wherein a reflective layer to reflect EUV light and an absorber layer to absorb EUV light, are formed in this order on a substrate made of e.g. glass. As the reflective layer, a multilayer reflective film having a high refractive index layer and a low refractive index layer alternately stacked is commonly used. In the multilayer reflective film, a plurality of interfaces between a high refractive index layer and a low refractive index layer are present, and a high reflectivity is obtained by adjusting the thicknesses of the high refractive index layer and the low refractive index layer so that phases of weak reflected light resulting at the respective interfaces are the same. Thus, the high refractive index layer and the low refractive index layer constituting the multilayer reflective film are required to have a regular periodic structure of predetermined thicknesses. Further, on the outermost surface of the multilayer reflective film, a protective layer having a resistant to etching for the absorber layer patterning is formed in some cases. In the present invention, in a case where a protective layer is formed on the multilayer reflective film, the multilayer reflective film including a protective layer will be referred to as a multilayer reflective film. For the absorber layer, a material having a high absorption coefficient to EUV light, specifically e.g. a material containing Cr or Ta as the main component, is used. On the outermost surface of the absorber layer, a low reflective layer having a low reflectivity for the light having a wavelength of inspection light to be used for inspection after patterning, is formed in some cases so that the pattern shape will easily be detected by an inspection after patterning.

As defects problematic in an EUV mask blank, phase defects and amplitude defects are present. Local irregularities such as pits, scratches and foreign matters present on the substrate surface and foreign matters included in the multilayer reflective film cause disorder in the periodic structure of layers of the multilayer reflective film deposited thereon, and locally change the phase of EUV light reflected on a photomask set to an exposure machine. If a photomask using an EUV mask blank having phase defects is set to an EUV exposure machine and a pattern on such a photomask is transferred to a wafer, a pattern transferred to the wafer is an incomplete pattern different from the desired pattern. Accordingly, the number of phase defects of a predetermined size or larger should be 0. Further, foreign matters in the vicinity of the surface of the multilayer reflective film and foreign matters included in the absorber layer have a negative effect to absorb EUV light and thereby to decrease the intensity of EUV reflected light from the multilayer reflective film. Also if a photomask using an EUV mask blank having amplitude defects is set to an EUV exposure machine and a pattern on such a photomask is transferred to a wafer, a pattern transferred to the wafer is an incomplete pattern different from the desired pattern. Accordingly, the number of amplitude defects of a predetermined size or larger should also be 0.

As a method for inspecting an EUV mask blank for phase defects and amplitude defects, a dark field inspection method using EUV light and a bright field inspection method or a dark field inspection method using DUV (deep ultraviolet) light (wavelength: 150 to 380 nm) or visible light (wavelength: 380 to 600 nm) may be mentioned. In the bright field inspection method, inspection light is applied to an object to be inspected and the intensity of the obtained reflected light is measured. The intensity of reflected light from a portion where a defect is present and the intensity of reflected light from a normal portion where no defect is present are different from each other, and the difference correlates with the size of the defect, and therefore, by utilizing the difference, the location where the defect is present and the size of the defect are specified. Whereas by the dark field inspection method, inspection light is applied to an object to be inspected and the intensity of obtained scattered light is measured. The intensity of scattered light from a portion where a defect is present and the intensity of scattered light from a portion where no defect is present are different from each other, and the difference correlates with the size of the defect, and therefore, by utilizing the difference, the location where the defect is present an the size of the defect are specified.

The dark field inspection method using EUV light is useful as a phase defect inspection method after formation of the multilayer reflective film. Non-Patent Document 1 discloses that by the dark field inspection method using EUV light after formation of the multilayer reflective film, a convex phase defect having a full width of half maximum of 36 nm and a height of 1 nm can be detected. Assuming that such convex defects have a Gaussian function shape, the sphere equivalent volume diameter (the diameter when the volume of a defect is calculated as a sphere, hereinafter referred to as SEVD) of the defect as calculated in accordance with Non-Patent Document 4 is 14 nm, and thus a phase defect of a very small size can be detected. However, it is known that the sensitivity for detection of an amplitude defect resulting from a foreign matter in the vicinity of the surface of the multilayer reflective film, by the dark field inspection method using EUV light, is lower than the sensitivity for detection of a phase defect resulting from a local irregularity present on the substrate surface or a foreign matter included in the multilayer reflective film. Specifically, Non-Patent Document 2 discloses that the minimum size of an amplitude defect which can stably be detected by the dark field inspection method using EUV light is 100 nm, which is 7 times the above-described detection limit size of a phase defect, and the sensitivity for detection of an amplitude defect tends to be insufficient.

Whereas, it is known that by the bright field inspection method or the dark field inspection method using DUV light or visible light, a phase defect and an amplitude defect can be detected at the same level of the sensitivity for detection. Specifically, Non-Patent Document 3 discloses that the minimum size of a phase defect which can stably be detected by the dark field inspection method at a wavelength of 266 nm is a convex defect having a full width of half maximum of 85 nm and a height of 2.7 nm. SEVD of such a defect obtained in accordance with the method disclosed in Non-Patent Document 4 is 35 nm. Whereas, the minimum size of an amplitude defect which can stably be detected by the dark field inspection method at a wavelength of 266 nm, as a result of evaluation using silica particles spread on the surface of the multilayer reflective film, is SEVD of 45 nm as reported in Non-Patent Document 3. Accordingly, the dark field inspection method at a wavelength of 266 nm is very superior in the sensitivity for detection of an amplitude defect to the dark field inspection method using EUV light, although it is inferior in the sensitivity for detection of a phase defect.

Accordingly, the dark field inspection method using EUV light is excellent in detectability of phase defects but is inferior in detectability of amplitude defects, whereas the bright field inspection method or the dark field inspection method using DUV light or visible light has detectabilities of amplitude defects and phase defects at the same level, but is inferior in the detectability of phase defects to the dark field inspection method using EUV light. Thus, there has been no method for stably detecting both phase defects and amplitude defects. To overcome such a problem, Patent Document 1 discloses a method for inspecting an EUV mask or an EUV mask blank for phase defects and amplitude defects by carrying out both dark field inspection method using EUV light and dark field inspection method using DUV light by an EUV mask inspection apparatus provided with both EUV light source and DUV light source.

PRIOR ART DOCUMENTS

Patent Documents

Patent Document 1: JP-A-2013-80810
Non-Patent Document 1: T. Yamane, et. al., "Defect detection sensitivity improvement of actinic blank inspection", 2011 International Symposium on Extreme Ultraviolet Lithography
Non-Patent Document 2: Tsuneo Terasawa et. al., "High Speed Actinic EUV Mask Blank Inspectio with Dark-Field Imaging", Proc. SPIE Vol. 5446, (2004), 804.
Non-Patent Document 3: Andy Ma, et. al., "Improvement of EUVL Mask Blank Defect Inspection Capability at Intel", Proc. SPIE Vol. 7379, (2009)
Non-Patent Document 4: Sungmin Huh, "Printability and inspectability of defects on the EUV mask for sub-32 nm half pitch HVM applicaiton", Proc. SPIE Vol. 7379 (2011)

DISCLOSURE OF INVENTION

Technical Problem

Foreign matters present on the substrate surface and foreign matters included in various films, which cause phase defects and amplitude defects, are derived from production apparatus, members used and atmosphere in a process for producing an EUV mask blank, and their chemical components are various. Specifically, convex foreign matters present on the substrate surface and foreign matters included in the multilayer reflective film to be phase defects and foreign matters in the vicinity of the surface of the multilayer reflective film to be amplitude defects, are considered to be metal foreign matters such as stainless steel, inorganic foreign matters such as glass, organic foreign matters such as carbon, and the like. In the case of a phase defect due to a convex foreign matter present on the substrate surface or a foreign matter included in the multilayer reflective film, the foreign matter is covered with the multilayer film, and at a stage where the defect is to be detected, the chemical component on the surface at a portion where the defect is present is the same as that at a normal portion where no defect is present. Accordingly, in the case of detecting phase defects, the detectability is univocally determined by the sizes of foreign matters constituting the phase defects regardless of the chemical component of the foreign matters. However, in a case where amplitude defects on a substrate with multilayer reflective film are to be detected by the bright field inspection method or the dark field inspection method using DUV light, since the defects are exposed to the surface of an object to be inspected, even though the foreign matters have the same size, the amount of change of the intensity of scattered light, reflected light and transmitted light by the amplitude defects varies depending upon the component of the foreign matters. Accordingly, although the locations of amplitude defects can be detected, their sizes cannot necessarily be accurately obtained. That is, usually, organic foreign matters have relatively high absorption ratio and refractive index for DUV light as compared with inorganic foreign matters such as a metal, organic foreign matters have a small influence over scattered light, reflected light and transmitted light as compared with inorganic foreign matters, the amount of change of scattered light, reflected light and transmitted light by organic foreign matters is small as compared with that by inorganic foreign matters. Thus, a defect resulting from an organic foreign matter is detected as a defect of a size smaller than the actual size as compared with a defect resulting from an inorganic foreign matter, even though they have the same size, and the size of a defect resulting from an organic foreign matter is underestimated. As a specific example, silica spheres and polystyrene latex resin spheres having known diameters are attached to the surface of a multilayer reflective film, and an inspection is carried out by using a dark field inspection apparatus (M1350 manufactured by Lasertec Corporation) using visible light having a wavelength of 488 nm, and the obtained relation between the amount of change of the intensity of scattered light due to the spheres on the surface of the multilayer reflective film, and the diameter of the sphere, is shown in FIG. 4. By comparison between the diameters of the silica spheres and the polystyrene latex resin spheres detected with the same amount of change of the intensity of scattered light, the diameter of the silica sphere is larger than the diameter of the polystyrene latex resin sphere, and a difference between the diameters is confirmed. Accordingly, in a case where an inspection of a substrate with multilayer reflective film for amplitude defects is carried out, it is difficult to estimate accurate sizes of amplitude defects, and there is a risk of flow of blanks having unacceptable amplitude defects into a photomask production process.

In order to solve such problems of the prior art, it is an object of the present invention to provide a process for inspecting an EUV mask blank capable of efficiently detecting phase defects and amplitude defects and accurately estimating the sizes of the amplitude defects, whereby flow of an EUV mask blank having unacceptable amplitude defects can be prevented, a process for producing an EUV mask blank using the inspection process, and an EUV mask blank.

Solution to Problem

In order to accomplish the above object, the present invention provides a process for inspecting an EUV mask blank having a multilayer reflective film for reflecting EUV light and an absorber layer for absorbing EUV light formed in this order on a substrate, which comprises:

a first defect distribution storing step of detecting an in-plane distribution of defects in the multilayer reflective film by, at a stage where the multilayer reflective film is formed on the substrate, applying EUV light to the surface of the multilayer reflective film and storing the detected first defect in-plane distribution data, a second defect distribution storing step of detecting an in-plane distribution of defects from the absorber layer by, at a stage where the absorber layer is formed on the multilayer reflective film, applying light having a wavelength of from 150 to 600 nm to the surface of the absorber layer and storing the detected second defect in-plane distribution data, and a defect distinguishing step of distinguishing phase defects and amplitude defects in the EUV mask blank by comparison between the first defect in-plane distribution data and the second defect in-plane distribution data.

In the process for inspecting an EUV mask blank of the present invention, a protective layer for the multilayer reflective film is further formed between the multilayer reflective film and the absorber layer of the EUV mask blank, and the first defect distribution storing step is carried out at a stage where the protective layer for the multilayer reflective film is formed.

In the process for inspecting an EUV mask blank of the present invention, a low reflective layer for inspection light to be used for inspection of a mask pattern is further formed on the absorber layer of the EUV mask blank, and the second defect distribution storing step is carried out at a stage where the low reflective layer is formed.

The present invention further provides a process for inspecting an EUV mask blank having a multilayer reflective film for reflecting EUV light, a protective layer for the multilayer reflective film and an absorber layer for absorbing EUV light formed in this order on a substrate, which comprises:

a first defect distribution storing step of detecting an in-plane distribution of defects in the multilayer reflective film and the protective layer of the multilayer reflective film by, at a stage where the multilayer reflective film and the protective layer for the multilayer reflective film are formed on the substrate, applying EUV light to the surface of the protective layer of the multilayer reflective film and storing the detected first defect in-plane distribution data, a second defect distribution storing step of detecting an in-plane distribution of defects from the absorber layer by, at a stage where the absorber layer is formed on the protective layer of the multilayer reflective film, applying light having a wavelength of from 150 to 600 nm to the surface of the absorber layer and storing the detected second defect in-plane distribution data, and a defect distinguishing step of distinguishing phase defects and amplitude defects in the EUV mask blank by comparison between the first defect in-plane distribution data and the second defect in-plane distribution data.

The present invention further provides a process for inspecting an EUV mask blank having a multilayer reflective film for reflecting EUV light, a protective layer for the multilayer reflective film, an absorber layer for absorbing EUV light and a low reflective layer for inspection light to be used for inspection of a mask pattern formed in this order on a substrate, which comprises:

a first defect distribution storing step of detecting an in-plane distribution of defects in the multilayer reflective film and the protective layer on the multilayer reflective film by, at a stage where the multilayer reflective film and the protective layer for the multilayer reflective film are formed on the substrate, applying EUV light to the surface of the protective layer of the multilayer reflective film and storing the detected first defect-in-plane distribution data, a second defect distribution storing step of detecting an in-plane distribution of defects from the absorber layer and the low reflective layer by, at a stage where the absorber layer and the low reflective layer are formed on the protective layer of the multilayer reflective film, applying light having a wavelength of from 150 to 600 nm to the surface of the low reflective layer and storing the detected second defect in-plane distribution data, and a defect distinguishing step of distinguishing phase defects and amplitude defects in the EUV mask blank by comparison between the first defect in-plane distribution data and the second defect in-plane distribution data.

The present invention further provides a process for producing an EUV mask blank, which comprises:

a step of forming a multilayer reflective film for reflecting EUV light on a substrate, a first defect distribution storing step of detecting an in-plane distribution of defects in the multilayer reflective film by applying EUV light to the surface of the multilayer reflective film and storing the detected first defect in-plane distribution data, a step of forming an absorber layer for absorbing EUV light on the multilayer reflective film, a second defect distribution storing step of detecting an in-plane distribution of defects from the absorber layer by applying light having a wavelength of from 150 to 600 nm to the surface of the absorber layer and storing the detected second defect in-plane distribution data, and a defect distinguishing step of distinguishing phase defects and amplitude defects in the EUV mask blank by comparison between the first defect in-plane distribution data and the second defect in-plane distribution data.

The process for producing an EUV mask blank of the present invention may further have a step of forming a protective layer for the multilayer reflective film on the multilayer reflective film. In such a case, the first defect distribution storing step is carried out after the step of forming the protective layer.

The process for producing an EUV mask blank of the present invention may further have a step of forming a low reflective layer for inspection light to be used for inspection of a mask pattern on the absorber layer of the EUV mask blank. In such a case, the second defect distribution storing step is carried out after the step of forming the low reflective layer.

In the process for producing an EUV mask blank of the present invention, the pressure in the step of forming the absorber layer is preferably at least $3.0 \times 10^{-2}$ [Pa] and at most $1.5 \times 10$ [Pa].

In the process for producing an EUV mask blank of the present invention, the light reflectivity of the absorber layer at a wavelength of inspection light within a wavelength range of from 150 to 600 nm is preferably at least 20%.

In the process for producing an EUV mask blank of the present invention, the angle of growth of defects in the absorber layer is preferably at least 0 [deg].

In the process for producing an EUV mask blank of the present invention, the root mean square roughness Rq of the surface of the multilayer reflective film is preferably at most 0.30 [nm], and the root mean square roughness Rq of the surface of the absorber layer is preferably at most 0.50 [nm].

Further, the present invention provides an EUV mask blank having a multilayer reflective film for reflecting EUV light and an absorber layer for absorbing EUV light formed in this order on a substrate, wherein the ratio of the size of a local irregularity on the surface of the absorber layer resulting from an amplitude defect present in the vicinity of the surface of the multilayer reflective film, to the size of the amplitude defect, i.e. the base layer defect size increase ratio, is at least 1 and at most 2.

The EUV mask blank of the present invention has the above base layer defect size increase ratio of preferably at least 1 and at most 1.5.

Advantageous Effects of Invention

By the process for inspecting an EUV mask blank of the present invention, a dark field inspection using EUV light is carried out at a stage where a multilayer reflective film is formed on a substrate, and a bright field inspection or dark field inspection using DUV light or visible light is carried out at a stage where an absorber layer is formed on the multilayer reflective film, and accordingly phase defects and amplitude defects can be distinguished with high accuracy, and every amplitude defect of an acceptable size or larger can be detected. The amplitude defects detected by the inspection process of the present invention can be corrected by a known method by e.g. focused ion beam, electron beam or an atomic force microscope in a photomask production process, and accordingly by the present invention, an EUV mask blank having no amplitude defects of an acceptable size or larger which cannot be corrected, can be obtained.

DESCRIPTION OF EMBODIMENTS

Now, the process for inspecting an EUV mask blank and the process for producing an EUV mask blank of the present invention will be described with reference to the drawings.

Figure 1:
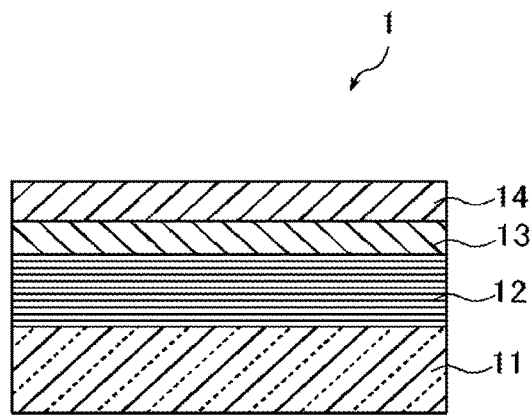
FIG. 1 is a schematic cross-sectional view illustrating an embodiment of an EUV mask blank to be inspected or to be produced by the process of the present invention.

FIG. 1 is a schematic cross-sectional view illustrating an embodiment of an EUV mask blank to be inspected or to be produced by the process of the present invention. An EUV mask blank 1 shown in FIG. 1 has a multilayer reflective film 12 for reflecting EUV light and an absorber layer 14 for absorbing EUV light formed in this order on a substrate 11. The multilayer reflective film 12 has a low refractive index layer with a low refractive index to EUV light and a high refractive index layer with a high refractive index to EUV light, alternately stacked plural times, to have a high EUV reflectivity. Between the multilayer reflective film 12 and the absorber layer 14, a protective layer 13 is formed for protecting the multilayer reflective film 12 at the time of forming a pattern in the absorber layer 14.

Here, in the EUV mask blank of the present invention, in the construction as shown in FIG. 1, only the substrate 11, the multilayer reflective film 12 and the absorber layer 14 are essential, and the protective layer 13 is an optional constituting element. Now, the individual constituting elements of the mask blank 1 will be described.

The substrate 11 is required to satisfy the properties as a substrate for an EUV mask blank.

Therefore, the substrate 11 is preferably one having a low thermal expansion coefficient (preferably $0 \pm 1.0 \times 10^{-7}$/° C., more preferably $0 \pm 0.3 \times 10^{-7}$/° C., further preferably $0 \pm 0.2 \times 10^{-7}$/° C., still further preferably $0 \pm 0.1 \times 10^{-7}$/° C., particularly preferably $0 \pm 0.05 \times 10^{-7}$/° C.) and being excellent in smoothness, planarity and durability against a cleaning liquid to be used for e.g. cleaning a mask blank or a photomask after patterning. As the substrate 11, specifically, a glass having a low thermal expansion coefficient, such as a $SiO_2$—$TiO_2$ type glass, may be used. However, the substrate is not limited thereto, and it is possible to employ a substrate of e.g. crystallized glass having β-quartz solid solution precipitated, quartz glass, silicon, or a metal. Further, a film such as a stress correcting film may be formed on the substrate 11.

The substrate 11 preferably has a smooth surface having a surface roughness of at most 0.15 nm, whereby phase defects of small sizes can be detected in the after-mentioned first defect distribution storing step. Further, the substrate 11 preferably has a flatness of at most 100 nm, whereby an excellent pattern transfer precision can be attained by a photomask after forming a pattern.

The size, thickness, etc. of the substrate 11 may suitably be determined depending upon e.g. the designed values for the mask. In Examples given hereinafter, a $SiO_2$—$TiO_2$ type glass having a size of 6 inches (152.4 mm) square and a thickness of 0.25 inch (6.3 mm) is used.

The property particularly required for the multilayer reflective layer 12 of the EUV mask blank is that a high EUV light reflectivity is obtained. Specifically, when light within the EUV wavelength region is applied at an incident angle of 6° to the surface of the multilayer reflective film 12, the maximum value of the reflectivity of light in the vicinity of a wavelength of 13.5 nm, is preferably at least 60%, more preferably at least 63%, further preferably at least 64%. Further, also in a case where a protective layer 13 is formed on the multilayer reflective layer 12, the maximum value of the reflectivity of light in the vicinity of a wavelength of 13.5 nm is preferably at least 60%, more preferably at least 63%, further preferably at least 64%.

As the multilayer reflective film 12 which satisfies the above properties, it is most common to use a Mo/Si multilayer reflective film having a Mo layer and a Si layer alternately stacked. However, the multilayer reflective film is not limited to such a film, and it may, for example, be a Be/Mo multilayer reflective film having a Be layer and a Mo layer alternately stacked, a Si compound/Mo compound multilayer reflective film having a Si compound layer and a Mo compound layer alternately stacked, a Si/Mo/Ru multilayer reflective film having a Si layer, a Mo layer and a Ru layer stacked in this order, or a Si/Ru/Mo/Ru multilayer reflective film having a Si layer, a Ru layer, a Mo layer and a Ru layer stacked in this order.

The thicknesses of the respective layers constituting the multilayer reflective film 12 and the stacked number of repeating units may suitably be selected depending upon the materials for the respective layers and the EUV light reflectivity required for the reflective layer. In the case of the Mo/Si multilayer reflective film as an example, in order to achieve the maximum value of the reflectivity of light in the vicinity of a wavelength of 13.5 nm of at least 60%, a Mo layer having a thickness of 2.3±0.1 nm and a Si layer having a thickness of 4.5±0.1 nm are stacked so that the stacked number of repeating units would be from 30 to 60.

In order to achieve the high EUV reflectivity and detectability of phase defects required in the first defect distribution storing step described hereinafter, the surface of the multilayer reflective film 12 is preferably smooth. Specifically, the root mean square roughness Rq of the surface of the multilayer reflective film 12 is preferably at most 0.30 nm, more preferably at most 0.25 nm, further preferably at most 0.20 nm.

In a case where a protective layer 13 is formed on the multilayer reflective film 12, the root mean square roughness Rq of the surface of the protective layer 13 preferably satisfies the above range.

In the process for producing an EUV mask blank of the present invention, the multilayer reflective film 12 is formed on a film-forming surface of the substrate 11. The procedure of forming the multilayer reflective film 12 on the film-forming surface of the substrate 11 may be a procedure commonly carried out in formation of a multilayer reflective film by an ion beam sputtering method or a magnetron sputtering method.

For example, in the case of forming a Mo/Si multilayer reflective film by means of an ion beam sputtering method, it is preferred that a Mo layer is formed to have a thickness of 2.3 nm at an ion accelerating voltage of from 300 to 1,500 V and a film-deposition rate of from 0.03 to 0.30 nm/sec by using a Mo target as the target and an Ar gas (gas pressure: $1.3 \times 10^{-2}$ Pa to $2.7 \times 10^{-2}$ Pa) as the sputtering gas, and then, a Si layer is formed to have a thickness of 4.5 nm at an ion accelerating voltage of from 300 to 1,500 V and a film-deposition rate of from 0.03 to 0.30 nm/sec by using a Si target as the target and an Ar gas (gas pressure: $1.3 \times 10^{-2}$ Pa to $2.7 \times 10^{-2}$ Pa) as the sputtering gas. When this operation is taken as one cycle, the Mo/Si multilayer reflective film is formed by stacking the Mo layer and the Si layer by from 40 to 50 cycles. In formation of the multilayer reflective film 12, in order to obtain a uniform film, the film is preferably formed while the substrate 11 is rotated using a rotator.

The protective layer 13 is provided for the purpose of protecting the multilayer reflective film 12, so that at the time of forming a pattern on the absorber layer 14 by an etching process, usually by a dry etching process, the multilayer reflective film 12 will not be damaged by the etching process. Accordingly, as the material for the protective layer, a material hardly susceptible to an influence by the etching process of the absorber layer 14 i.e. having an etching rate slower than the absorber layer 14 and hardly susceptible to damage by such an etching process, is selected. The protective layer is preferably made of Ru or a Ru compound (such as RuN, RuB, RuSi or RuNb) as the constituting material.

In a case where the EUV mask blank 1 of the present invention has a structure such that it has the protective layer 13 between the multilayer reflective film 12 and the absorber layer 14, the after-mentioned first defect distribution storing step is carried out after the protective layer 13 is formed on the multilayer reflective film 12.

The protective layer 13 is formed by a known film-forming method such as a magnetron sputtering method or an ion beam sputtering method. In the case of forming a Ru film by means of a magnetron sputtering method, it is preferred that a Ru film is formed to have a thickness of from 2 to 5 nm at an applied voltage of from 30 V to 1,500 V and a film-deposition rate of from 0.02 to 1.0 nm/sec by using a Ru target as the target and an Ar gas (gas pressure: $1.0 \times 10^{-2}$ Pa to $10 \times 10^{-1}$ Pa) as the sputtering gas.

In the present invention, the first defect distribution storing step is carried out at a stage where the multilayer reflective film is formed on the substrate. In the first defect distribution storing step, an in-plane distribution of phase defects in the multilayer reflective film is detected by applying EUV light to the surface of the multilayer reflective film, and the detected first defect in-plane distribution data is stored.

In the first defect distribution storing step, as a procedure of applying EUV light to the surface of the multilayer reflective film to detect an in-plane distribution of phase defects in the multilayer reflective film, a procedure commonly carried out in the dark field inspection method using EUV light may be employed. In the dark field inspection method using EUV light, EUV light is applied from a vertical direction or from an oblique direction to the surface of the multilayer reflective film (in a case where a protective film is formed on the multilayer reflective film, to the surface of the protective layer). If a phase defect is present in the multilayer reflective film (in a case where a protective layer is formed on the multilayer reflective film, in the protective layer), the intensity of scattered light of EUV light is different from the intensity of scattered light from a normal portion where no phase defect is present, and accordingly by utilizing the change of the intensity of scattered light, the location of the phase defect in a horizontal direction can be obtained. Further, since the amount of change of the intensity of scattered light correlates with the size of the phase defect, information about the relative size of the defect can be obtained. Accordingly, in the first defect distribution storing step, phase defects are detected, and an in-plane distribution of the detected phase defects i.e. coordinates where the phase defects are present and their relative size information are stored.

The dark field inspection method using EUV light is disclosed in Patent Document 1, JP-A-2013-24772 and JP-A-2013-19793, and the procedure may be carried out by reference to such documents.

In the present invention, after the first detect distribution storing step is carried out, an absorber layer 14 is formed on the multilayer reflective film 12 (in a case where a protective layer 13 is formed on the multilayer reflective film 12, on the protective layer 13).

The property particularly required for the absorber layer 14 of the EUV mask blank is that the EUV light reflectivity is very low. Specifically, the maximum light reflectivity in the vicinity of a wavelength of 13.5 nm at the time when light in the EUV wavelength region is applied to the surface of the absorber layer 3 is preferably at most 0.5%, more preferably at most 0.1%.

In order to attain the above property, the absorber layer 14 is made of a material having a high absorption coefficient to EUV light. As the material having a high absorption coefficient to EUV light, a material containing tantalum (Ta) as the main component is preferably used. In this specification, the material containing tantalum (Ta) as the main component is meant for a material containing at least 40 at % of Ta in the material. The absorber layer 3 preferably contains at least 50 at % of Ta, more preferably at least 55 at %.

The material containing Ta as the main component to be used for the absorber layer 14 preferably contains, in addition to Ta, at least one component of hafnium (Hf), silicon (Si), zirconium (Zr), germanium (Ge), boron (B), palladium (Pd), hydrogen (H) and nitrogen (N). The material containing the above element in addition to Ta may, for example, be specifically TaN, TaNH, TaHf, TaHfN, TaBSi, TaBSiN, TaB, TaBN, TaSi, TaSiN, TaGe, TaGeN, TaZr, TaZrN, TaPd or TaPdN.

The thickness of the absorber layer 14 is preferably within a range of from 20 to 100 nm.

If the surface roughness of the absorber layer 14 is large, the sensitivity for detection of an in-plane distribution of defects in the second defect distribution storing step described hereinafter will be lowered. Further, the edge roughness of a pattern to be formed on the absorber layer 14 tends to be large, and the dimensional precision of the pattern tends to be poor. From such reasons, the surface of the absorber layer 14 is preferably smooth. Specifically, the root mean square roughness Rq of the surface of the absorber layer 14 is preferably at most 0.50 nm, more preferably at most 0.40 nm, further preferably at most 0.30 nm.

[Film-Forming Conditions for Absorber Layer]

The absorber layer 14 is formed by a well-known film-forming method such as a magnetron sputtering method or an ion beam sputtering method. In either film-forming method, formation of the absorber layer 14 is carried out in a reduced pressure environment, and in order that amplitude defects present in the vicinity of the surface of the multilayer reflective film are stably detected in the second defect distribution storing step, formation of the absorber layer 14 is preferably carried out under a predetermined pressure. Specifically, it is preferably carried out in a reduced pressure environment under a pressure of at least $3.0 \times 10^{-2}$ Pa and at most $1.5 \times 10$ Pa. Formation of the absorber layer 14 in a reduced pressure environment under a pressure of at least $3.0 \times 10^{-2}$ Pa is preferred, whereby the base layer defect size increase ratio of the absorber layer 14 is 1 or higher. Here, the base layer defect size increase ratio is a ratio of the SEVD size of a local irregularity on the surface of the absorber layer resulting from an amplitude defect present in the vicinity of the surface of the multilayer reflective film, to the SEVD size of the amplitude defect. The reason is as follows. In a reduced pressure environment under a pressure of at least $3.0 \times 10^{-2}$ Pa, film-forming particles sputtered from a target have a kinetic energy in a direction horizontal to the substrate by collisions with process gas particles, and the amount of the film-forming particles which enter the substrate from an oblique direction increases, and accordingly the film is isotropically deposited on the amplitude defects present in the vicinity of the surface of the multilayer reflective film. However, if the absorber layer 14 is formed in a reduced pressure environment under a pressure exceeding $1.5 \times 10$ Pa, after the film-form ing particles collide with process gas particles, they return to and are attached to the surface of the target, and may be a dust source, such being unfavorable. Formation of the absorber layer 14 is preferably carried out in a reduced pressure environment under a pressure of at least $1.0 \times 10^{-1}$ Pa and at most $8.0 \times 10^{-1}$ Pa, whereby the base layer defect size increase ratio can be at least 1 and at most 2, and is more preferably carried out in a reduced pressure environment under a pressure of at least $2.0 \times 10^{-1}$ Pa and at most $4.0 \times 10^{-1}$ Pa, whereby the base layer defect size increase ratio can be at least 1 and at most 1.5. Further, as a film-formation parameter of adjusting the base layer defect size increase ratio, a RF power may be mentioned in addition to the pressure. When the RF power is low, the same phenomenon as when the pressure is increased is expected, and the base layer defect size increase ratio tends to be high. The RF power is preferably from 500 to 3,000 W, particularly preferably from 500 to 1,500 W.

In the case of forming a TaN layer as the absorber layer 14 by means of a magnetron sputtering method, it is preferred to form a TaN layer to have a thickness of from 40 to 100 nm at a RF power of 1,000 W and a film-deposition rate of from 0.01 to 0.1 nm/sec by using a Ta target as the target and a $N_2$ gas (gas pressure: $1.8 \times 10^{-2}$ Pa to $2.7 \times 10^{-2}$ Pa) as the sputtering gas.

Figure 3:
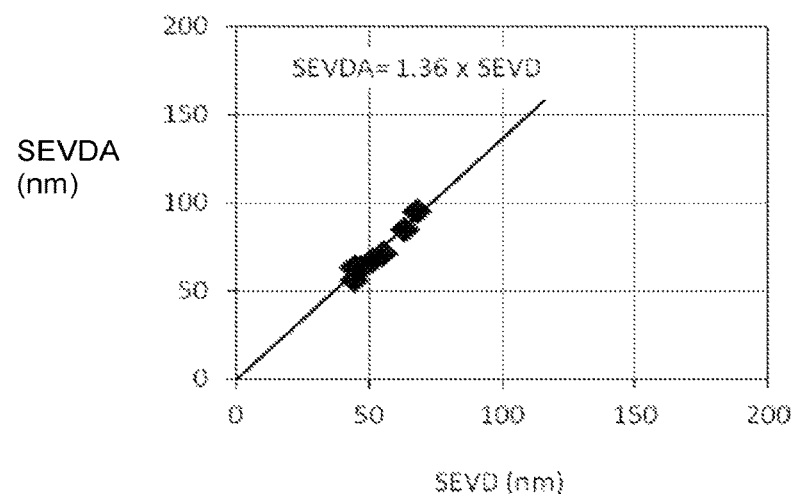
FIG. 3 is a diagram showing an example of the relation between the size of an amplitude defect present in the vicinity of the surface of a multilayer reflective film, and the size of a local irregularity on the surface of an absorber layer resulting from the above amplitude defect.
Figure 4:
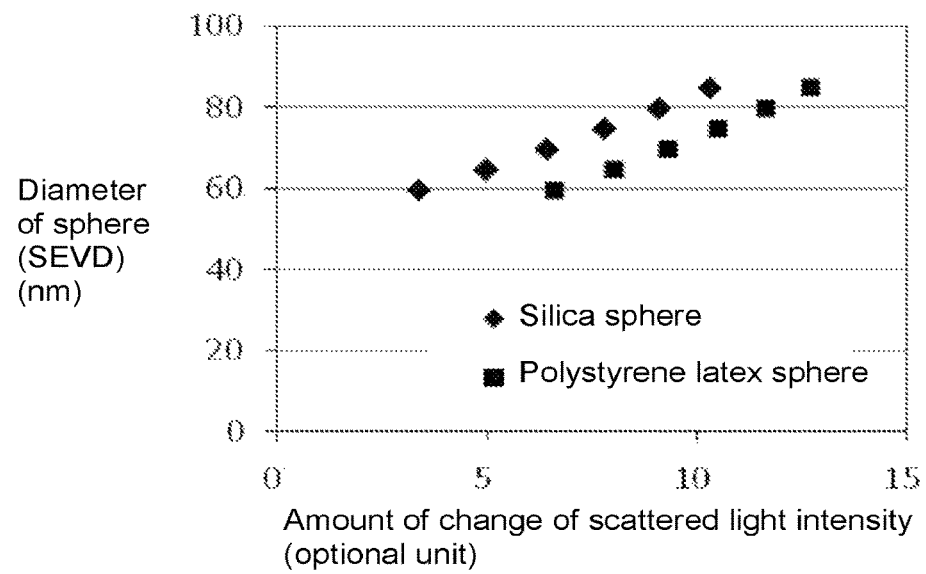
FIG. 4 is a diagram showing the relation between the amount of change of the intensity of scattered light due to a sphere on the surface of a multilayer reflective film, and the diameter of the sphere.

Specifically for example, a TaN layer as the absorber layer 14 is formed to have a thickness of 70 nm by means of a magnetron sputtering method at a RF power of 1,000 W and a film-deposition rate of 0.1 nm/sec by using a Ta target as the target and a $N_2$ gas (gas pressure: $2.3 \times 10^{-2}$ Pa) as the sputtering gas, the sizes of amplitude defects present in the vicinity of the surface of the multilayer reflective film and the sizes of local irregularities on the surface of the absorber layer resulting from the amplitude defects are measured by an atomic force microscope, and the result of comparison between them is shown in FIG. 3. The sizes of local irregularities on the surface of the absorber layer resulting from amplitude defects present in the vicinity of the surface of the multilayer reflective film are large as compared with the sizes of the amplitude defects, and the base layer defect size increase ratio is 1.36. Further, the base layer defect size increase ratio can be determined, instead of the method of measuring the sizes of the amplitude defects present in the vicinity of the surface of the multilayer reflective film before and after film formation of the absorber layer by an atomic force microscope, by a method in which the cross-sections of amplitude defects detected after film formation of the absorber layer are observed with a SEM, and the sizes of the amplitude defects present in the vicinity of the surface of the multilayer reflective film and the sizes of local irregularities on the surface of the absorber layer resulting from the amplitude defects are obtained, and the base layer defect size increase ratio is calculated from their ratio.

In formation of the absorber layer 14 by means of a sputtering method, in order to obtain a uniform film, the absorber layer 14 is preferably formed while the substrate 11 is rotated using a rotator.

In the present invention, the second defect distribution storing step is carried out at a stage where the absorber layer is formed on the multilayer reflective film. In the second defect distribution storing step, by applying light having a wavelength of from 150 to 600 nm to the surface of the absorber layer, amplitude defects resulting from foreign matters in the vicinity of the surface of the multilayer reflective film and foreign matters present inside the absorber layer are detected and in addition, some of phase defects detected in the first defect distribution storing step are detected, and the detected second defect in-plane distribution data is stored.

In the second defect distribution storing step, as the procedure of applying light having a wavelength of from 150 to 600 nm to the surface of the absorber layer to detect an in-plane distribution of amplitude defects, a procedure commonly carried out in the bright field inspection method or the dark field inspection method using DUV light or visible light may be employed. In the bright field inspection method using DUV light or visible light, light having a wavelength of from 150 to 600 nm is applied to the surface of the absorber layer, and the intensity of the specularly reflected light is measured. If a phase defect in the multilayer reflective film, an amplitude defect resulting from a foreign matter in the vicinity of the surface of the multilayer reflective film, or a foreign matter in the film or on the surface of the absorber layer is present, a local irregularity results on the surface of the absorber layer. The intensity of specularly reflected light from a portion where such a local irregularity is present is different from that at a normal portion where no local step is present, and accordingly by detecting the change of the intensity of specularly reflected light, the location of the defect can be detected. Here, since the difference between the intensity of specularly reflected light from a portion where a defect is present and the intensity of specularly reflected light from a normal portion where no defect is present, correlates with the size of the defect, the relative size of the defect can also be obtained from the amount of change of the intensity of specularly reflected light. Further, in the dark field inspection method using DUV light or visible light, light having a wavelength of from 150 to 600 nm is applied from a vertical direction or from an oblique direction to the surface of the absorber layer, and the intensity of the scattered light is measured. In the same manner as in the bright field inspection method, if a phase defect in the multilayer reflective film, an amplitude defect in the vicinity of the surface of the multilayer reflective film or a foreign matter in the film or on the surface of the absorber layer is present, a local irregularity results on the surface of the absorber layer, and the intensity of scattered light from a portion where such a local irregularity is present is different from the intensity of scattered light from a normal portion where no such step is present, and accordingly by utilizing such a change of the intensity of scattered light, the location of the defect can be detected. Further, since the difference between the intensity of scattered light from a portion where a defect is present and the intensity of scattered light from a normal portion where no defect is present correlates with the size of the defect, the relative size of the defect can also be obtained by measuring the amount of change of the intensity of scattered light.

The dark field inspection method using DUV light or visible light is disclosed in Patent Document 1, and the procedure may be carried out by reference to Patent Document 1.

In the second defect distribution storing step, light having a wavelength of from 150 to 600 nm is applied to the surface of the absorber layer, and by the change of the intensity of the specularly reflected light, an in-plane distribution of defects from the absorber layer is detected. Thus, the absorber layer 14 preferably has a high light reflectivity at a wavelength of inspection light within a wavelength range of from 150 to 600 nm. Specifically, it has a light reflectivity at a wavelength of inspection light within a wavelength range of from 150 to 600 nm of preferably at least 20%, more preferably at least 30%, further preferably at least 40%. However, a light reflectivity of at least 20% over the entire wavelength range of from 150 to 600 nm is not necessarily required, and the light reflectivity at a wavelength of inspection light, used in the second defect distribution storing step, is preferably at least 20%, more preferably at least 30%, further preferably at least 40%.

The second defect distribution storing step is carried out preferably after the absorber layer is formed and a step of removing foreign matters present on the surface of the absorber layer is carried out. As a method of removing foreign matters present on the surface of the absorber layer, a wet washing method using an acidic or alkaline chemical solution, a dry washing method using e.g. $CO_2$ snow or Ar snow (for example, Eco-Snow manufactured by Eco-Snow Systems) or a method using an atomic force microscope (for example, MeRiT manufactured by Rave) may, for example, be mentioned.

In the present invention, a defect distinguishing step is carried out. In the defect distinguishing step, the first defect in-plane distribution data obtained in the first defect distribution storing step and the second defect in-plane distribution data obtained in the second defect distribution storing step are compared to obtain amplitude defects in the EUV mask blank. That is, defects obtained in the first defect distribution storing step only include phase defects, whereas defects obtained in the second defect distribution storing step include not only amplitude defects but also the phase defects detected in the first defect distribution storing step, since the phase defects obtained in the first defect distribution storing step cause local steps in the form of irregularities on the surface of the absorber layer. Accordingly, by removing the defects obtained in the first defect distribution storing step from the defects obtained in the second defect in-plane distribution storing step, defect in-plane distribution data of only the amplitude defects, i.e. the coordinates where the amplitude defects are present and their relative size information can be obtained.

If the bright field inspection or dark field inspection using DUV light is carried out at a stage where the multilayer reflective film is formed to detect amplitude defects present in the vicinity of the surface of the multilayer reflective film as in the method for inspecting an EUV mask as disclosed in Patent Document 1, the amount of change of the intensity of specularly reflected light or the intensity of scattered light due to presence of amplitude defects, utilized in this inspection, depends on not only the sizes of the amplitude defects but also the chemical component of the amplitude defects, and thus the sizes of the amplitude defects cannot accurately be detected.

Whereas in the second defect distribution storing step of the present invention, a bright field inspection or dark field inspection using DUV light or visible light is carried out at a stage where the absorber layer is formed on the multilayer reflective film, and amplitude defects present in the vicinity of the surface of the multilayer reflective film are detected. In such a case, amplitude defects present in the vicinity of the surface of the multilayer reflective film cause local irregularities at the corresponding portion on the surface of the absorber layer via formation of the absorber layer on the multilayer reflective film, and by utilizing the change of the intensity of specularly reflected light or the intensity of scattered light due to the local irregularities as described above, the locations and the relative sizes of the amplitude defects are obtained by the bright field inspection or dark field inspection. Here, since the amplitude defects present in the vicinity of the surface of the multilayer reflective film are covered with the absorber layer, the amount of the change of the intensity of specularly reflected light or the intensity of scattered light due to presence of the amplitude defects, utilized in this inspection, only depends on the sizes of the amplitude defects and does not depend on the chemical component of the amplitude defects, and accordingly the sizes of the amplitude defects can stably be detected.

In addition, as compared with the sizes of the amplitude defects present in the vicinity of the surface of the multilayer reflective film, the sizes of the local irregularities at the corresponding portion formed on the surface of the absorber layer can be adjusted to be small or large by the film-forming conditions for the absorber layer. The ratio of the size of a local irregularity at a portion of an amplitude defect present in the vicinity of the surface of the multilayer reflective film as the base layer of the absorber layer, formed on the surface of the absorber layer after formation of the absorber layer, to the size of the amplitude defect, is defined as the base layer defect size increase ratio, and when the ratio is higher than 1, the size of the local irregularity at a portion of the amplitude defect present in the vicinity of the surface of the multilayer reflective film, formed on the surface of the absorber layer after formation of the absorber layer, is larger than the size of the amplitude defect. Further, on the contrary, if the ratio is smaller than 1, the size of the local irregularity at a portion of the amplitude defect present in the vicinity of the surface of the multilayer reflective film, formed on the surface of the absorber layer after formation of the absorber layer, is smaller than the size of the amplitude defect.

Here, amplitude defects of a predetermined size or smaller can be removed or corrected by a defect correction apparatus utilizing focused ion beam, electron beam or an atomic force microscope, specifically, MR8000 manufactured by Hitachi High-Tech Science Corporation, MeRiT manufactured by CarlZeiss or Merlin manufactured by Rave, in a photomask production process, and the resulting photomask can be used without any problem. Otherwise, a pattern formation position of a photomask is adjusted depending upon the locations of amplitude defects, that is, the amplitude defects are located within an area where the absorber layer of the photomask is present, whereby such a photomask can be used without any problem even though amplitude defects are present. Here, the size of a defect which can be removed or corrected is determined by the size of an amplitude defect present in the vicinity of the surface of the multilayer reflective film or the size of a foreign matter present in the absorber layer, not by the size of a local irregularity on the surface of the absorber layer. Thus, it is preferred to properly select film-forming conditions for the absorber layer so that the size of the local irregularity at a portion of an amplitude defect present in the vicinity of the multilayer reflective film, formed on the surface of the absorber layer, is relatively large as compared with the size of the amplitude defect, that is, the base layer defect size increase ratio is at least 1 and at most 2, further preferably at least 1 and at most 1.5. By adjusting the base layer defect size increase ratio to be within the above preferred range, amplitude defects of a predetermined size or larger can securely be detected in the second defect distribution storing step. Further, the film-forming conditions for the absorber layer to adjust the base layer detect size increase ratio to be within the above preferred range are shown in the above [Film-forming conditions for absorber layer].

In the present invention, in order that a photomask obtained by correction in the photomask production process can be used without any problem, the sizes and the number of amplitude defects distinguished in the defect distinguishing step should be at most predetermined values. Specifically, the sphere equivalent volume diameter on absorber film (the diameter when the volume of an absorber film surface on a defect is calculated as a sphere, hereinafter referred to as SEVDA) should satisfy the following formula (1), where P (nm) is the size of a circuit pattern to be formed on the photomask. For example, in a case where the width P of a circuit pattern to be formed on the photomask is 60 nm and the base layer defect size increase ratio is 1.2, the amplitude defect size distinguished in the defect distinguishing step of the present invention should be SEVDA≤50 nm. Here, for P, for example, the value of mask minimum primary feature size (nm) in International Technology Roadmap for Semiconductors, 2012, Table LITH6 should be referred to. For example, the value of P in the year 2016 is 55 nm.

$$SEVDA\text{(nm)} \leq P \times \text{base layer defect size increase ratio} \quad (1)$$

Further, in the present invention, the number of amplitude defects which are distinguished in the defect distinguishing step and have the sizes of SEVDA which satisfies the formula (1) should be at most 10, preferably at most 7, further preferably at most 5. If the number is larger than 10, correction in the photomask production process will take long, and there may be a risk such that the defects cannot successfully be corrected and the obtained photomask may not be used.

Further, an EUV mask blank to be inspected or to be produced by the process of the present invention may have a constituting element other than the construction shown in FIG. 1 (i.e. the substrate 11, the multilayer reflective film 12, the protective layer 13 and the absorber layer 14).

Figure 2:
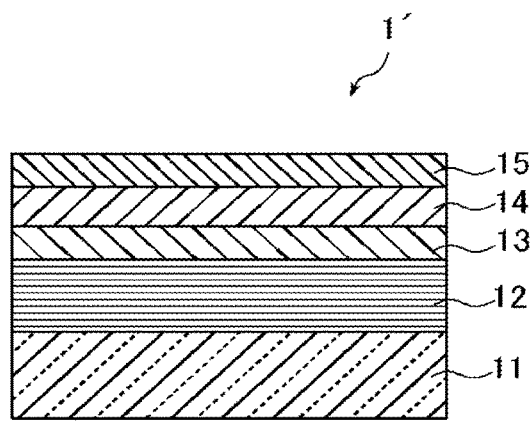
FIG. 2 is a schematic cross-sectional view illustrating another embodiment of an EUV mask blank to be inspected or to be produced by the process of the present invention.

FIG. 2 is a schematic cross-sectional view illustrating another embodiment of an EUV mask blank to be inspected or to be produced by the process of the present invention.

In an EUV mask blank 1' as shown in FIG. 2, a low reflective layer 15 for inspection light to be used for inspection of a mask pattern is formed on the absorber layer 14.

In the preparation of an EUV mask from the EUV mask blank to be inspected or to be produced by the process of the present invention, after forming a pattern in the absorber layer, inspection is carried out to see that this pattern is formed as designed. In this inspection of the mask pattern, usually an inspection machine using mask pattern inspection light of about 257 nm as mask pattern inspection light, is employed. That is, the inspection is made by the difference in reflectivity of such light of about 257 nm, specifically by the difference in the reflectivity between a surface exposed by removal of the absorber layer 14 by patterning and the surface of the absorber layer 14 remained without being removed by the patterning. Here, the former is the surface of the protective layer 13, and in a case where no protective layer 13 is formed on the multilayer reflective layer 12, it is the surface of the multilayer reflective layer 12.

Therefore, if the difference in the reflectivity between the protective layer 13 surface (or the reflective layer 12 surface) and the absorber layer 14 surface to the wavelength of mask pattern inspection light of about 257 nm, is too small, the contrast at the time of the inspection becomes poor, and an accurate inspection may not be possible.

The absorber layer 14 having the above-described construction has an extremely low EUV light reflectivity and has excellent properties as an absorber layer for an EUV mask blank, but from the viewpoint of the wavelength of mask pattern inspection light, the light reflectivity may not necessarily be sufficiently low. As a result, the difference between the reflectivity at the absorber layer 14 surface and the reflectivity at the protective layer 13 surface at the wavelength of inspection light, tends to be small, and the contrast at the time of inspection may not sufficiently be obtained. If the contrast at the time of inspection cannot be sufficiently obtained, at the protective layer 13 surface (or the multilayer reflective film 12 surface), a defect in the pattern cannot be sufficiently detected in the inspection of a mask, and an accurate inspection of a defect may not be carried out.

Like in the EUV mask blank 1' shown in FIG. 2, by forming a low reflective layer 15 on the absorber layer 14, the contrast at the time of inspection will be good. In other words, the light reflectivity at the wavelength of mask pattern inspection light becomes very low. With the low reflective layer 15 to be formed for such a purpose, the maximum light reflectivity at the wavelength of inspection light when irradiated with mask pattern inspection light, is preferably at most 15%, more preferably at most 10%, further preferably at most 5%.

When the light reflectivity at the wavelength of mask pattern inspection light at the low reflective layer 15 is at most 15%, the contrast at the time of the inspection will be good.

In this specification, the contrast is obtained by using the following formula (2).

$$\text{Contrast (\%)} = ((R_2 - R_1)/(R_2 + R_1)) \times 100 \quad (2)$$

Here, $R_2$ at the wavelength of mask pattern inspection light is the reflectivity at the protective layer 13 surface (or the multilayer reflective film 12 surface), and $R_1$ is the reflectivity at the surface of the low reflective layer 15. Here, the above $R_1$ and $R_2$ are measured in such a state that a pattern is formed in the absorber layer 14 and the low reflective layer 15 of the EUV mask blank 1' shown in FIG. 2. The above $R_2$ is a value measured at the protective layer 13 surface (or the multilayer reflective film 12 surface) exposed as the absorber layer 14 and the low reflective layer 15 are removed by patterning, and $R_1$ is a value measured at the surface of the low reflective layer 15 remaining without being removed by patterning.

In the present invention, the contrast represented by the above formula is more preferably at least 45%, further preferably at least 60%, particularly preferably at least 80%.

To attain the above-described properties, the low reflective layer 15 is preferably constituted by a material having a refractive index lower than the absorber layer 14 at the wavelength of inspection light, and its crystal state is preferably amorphous.

As a specific example of such a low reflective layer 15, a layer containing Ta and oxygen as the main component is preferred, and particularly a layer containing TaO, TaON, TaBO or TaBON as the main component may, for example, be mentioned. As another example, a layer containing TaBSiO or TaBSiON as the main component may be mentioned.

With the above-described construction, the low reflective layer (TaON, TaO, TaBON, TaBO, TaBSiO or TaBSiON) is amorphous in its crystal state and is excellent in its surface smoothness. Specifically, the root mean square roughness Rq of the low reflective layer surface is at most 0.5 nm.

As mentioned above, in order to secure the sensitivity for detecting an in-plane distribution of defects in the second defect distribution storing step and to prevent deterioration in the dimensional precision of a pattern due to an influence of the edge roughness, it is required that the absorber layer 14 surface is smooth. The low reflective layer 15 is formed on the absorber layer 15, and therefore, for the same reason, its surface is required to be smooth.

When the root mean square roughness Rq of the low reflective layer 15 surface is at most 0.5 nm, the low reflective layer 15 surface is sufficiently smooth and free from deterioration in the dimensional precision of a pattern due to an influence of the edge roughness. The root mean square roughness of the low reflective layer 15 surface is more preferably at most 0.4 nm, further preferably at most 0.3 nm.

In a case where the low reflective layer 15 is formed on the absorber layer 14, the total thickness of the absorber layer 14 and the low reflective layer 15 is preferably from 51 to 130 nm. Further, if the thickness of the low reflective layer 15 is more than the thickness of the absorber layer 14, the EUV absorbing property at the absorber layer 14 is likely to be low, and therefore, the thickness of the low reflective layer 15 is preferably less than the thickness of the absorber layer 14. For this reason, the thickness of the low reflective layer 15 is preferably from 1 to 30 nm, more preferably from 2 to 20 nm.

The low reflective layer (TaO, TaON, TaBO, TaBON, TaBSiO or TaBSiON) may be formed by a film-forming method, e.g. a sputtering method such as a magnetron sputtering method or an ion beam sputtering method.

In a case where an EUV mask blank to be inspected or to be produced by the process of the present invention is the mask blank 1' shown in FIG. 2, the second defect distribution storing step is carried out at a stage where the low reflective layer 15 is formed. Accordingly, in the second defect distribution storing step, light having a wavelength of from 150 to 600 nm is applied to the surface of the low reflective layer 15 to detect an in-plane distribution of defects from the low reflective layer 15, and the detected second defect in-plane distribution data is stored. Defects to be detected in the second defect distribution storing step include phase defects by disorder of the multilayer reflective film periodic structure, amplitude defects present in the vicinity of the surface of the multilayer reflective film which appear as phase defects or amplitude defects on the surface of the low reflective layer, foreign matters present inside the absorber layer or inside the low reflective layer, and amplitude defects resulting from foreign matters present on the surface of the low reflective layer.

In the case of the mask blank 1' shown in FIG. 2, the low reflective layer 15 preferably has a high light reflectance at a wavelength of inspection light within a wavelength range of from 150 to 600 nm. Specifically, it has a light reflectance at a wavelength of inspection light within a wavelength range of from 150 to 600 nm of preferably at least 20%, more preferably at least 30%, further preferably at least 40%.

Here, the reason as to why it is preferred to form the low reflective layer 15 on the absorber layer 14 as in the EUV mask blank 1' shown in FIG. 2, is that the wavelength of mask pattern inspection light is different from the wavelength of EUV light. Therefore, in a case where EUV light (in the vicinity of 13.5 nm) is used as the mask pattern inspection light, it is considered unnecessary to form a low reflective layer 15 on the absorber layer 14. The wavelength of mask pattern inspection light tends to be shifted toward a low wavelength side as the size of a pattern becomes small, and in future, it is considered to be shifted to 193 nm or further to 13.5 nm. Further, in the case where the wavelength of inspection light is 193 nm, it may not be required to form a low reflective layer 15 on the absorber layer 14. In the case where the wavelength of mask pattern inspection light is 13.5 nm, it is considered unnecessary to form a low reflective layer 15 on the absorber layer 14.

EXAMPLES

Now, the present invention will be described in further detail with reference to Examples. However, it should be understood that the present invention is by no means restricted thereto.

Reference Example

Figure 5:
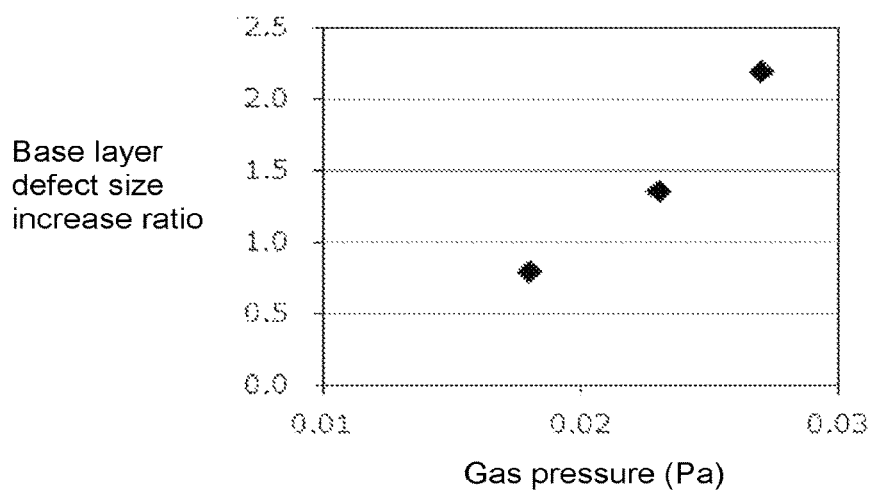
FIG. 5 is a diagram illustrating an example of the relation between the gas pressure and the base layer defect size increase ratio.

Sizes of amplitude defects present in the vicinity of the surface of a multilayer reflective film are measured by an atomic force microscope, and then by means of a magnetron sputtering method, TaN layers as the absorber layer 14 are formed to have a thickness of 70 nm at a RF power of 1,000 W by using a Ta target as the target and a $N_2$ gas as the sputtering gas under various different gas pressures. The sizes of local irregularities on the surface of the absorber layer resulting from amplitude defects present in the vicinity of the surface of the multilayer reflective film, the sizes of which are measured before the absorber layer is formed, are measured again by an atomic force microscope, and the sizes between before and after formation of the absorber layer are compared, whereby the base layer defect size increase ratio is obtained. The dependence of the base layer defect size increase ratio on the gas pressure is shown in FIG. 5. It is possible to adjust the base layer defect size increase ratio to be within a predetermined range by adjusting the gas pressure to be within a proper range.

The entire disclosure of Japanese Patent Application No. 2014-213394 filed on Oct. 20, 2014 including specification, claims, drawings and summary is incorporated herein by reference in its entirety.

What is claimed is:

1. A process for inspecting a reflective mask blank for EUV lithography having a multilayer reflective film for reflecting EUV light and an absorber layer for absorbing EUV light formed in this order on a substrate, which comprises:
    a first defect distribution storing step of detecting an in-plane distribution of defects in the multilayer reflective film by, at a stage where the multilayer reflective film is formed on the substrate, applying EUV light to the surface of the multilayer reflective film and storing the detected first defect in-plane distribution data,
    a second defect distribution storing step of detecting an in-plane distribution of defects from the absorber layer by, at a stage where the absorber layer is formed on the multilayer reflective film, applying light having a wavelength of from 150 to 600 nm to the surface of the absorber layer and storing the detected second defect in-plane distribution data, and
    a defect distinguishing step of distinguishing phase defects and amplitude defects in the reflective mask blank for EUV lithography by comparison between the first defect in-plane distribution data and the second defect in-plane distribution data.

2. The process for inspecting a reflective mask blank for EUV lithography according to claim 1, wherein a protective layer for the multilayer reflective film is further formed between the multilayer reflective film and the absorber layer of the reflective mask blank for EUV lithography, and the first defect distribution storing step is carried out at a stage where the protective layer for the multilayer reflective film is formed.

3. The process for inspecting a reflective mask blank for EUV lithography according to claim 1, wherein a low reflective layer for inspection light to be used for inspection of a mask pattern is further formed on the absorber layer of the reflective mask blank for EUV lithography, and the second defect distribution storing step is carried out at a stage where the low reflective layer is formed.

4. A process for producing a reflective mask blank for EUV lithography, which comprises:
    a step of forming a multilayer reflective film for reflecting EUV light on a substrate,
    a first defect distribution storing step of detecting an in-plane distribution of defects in the multilayer reflective film by applying EUV light to the surface of the multilayer reflective film and storing the detected first defect in-plane distribution data,
    a step of forming an absorber layer for absorbing EUV light on the multilayer reflective film,
    a second defect distribution storing step of detecting an in-plane distribution of defects from the absorber layer by applying light having a wavelength of from 150 to 600 nm to the surface of the absorber layer and storing the detected second defect in-plane distribution data, and
    a defect distinguishing step of distinguishing phase defects and amplitude defects in the reflective mask blank for EUV lithography by comparison between the first defect in-plane distribution data and the second defect in-plane distribution data.

5. The process for producing a reflective mask blank for EUV lithography according claim 4, which further has a step of forming a protective layer for the multilayer reflective film on the multilayer reflective film, and wherein the first defect distribution storing step is carried out after the step of forming the protective layer.

6. The process for producing a reflective mask blank for EUV lithography according to claim 4, which further has a step of forming a low reflective layer for inspection light to be used for inspection of a mask pattern, on the absorber layer of the reflective mask blank for EUV lithography, and wherein the second defect distribution storing step is carried out after the step of forming the low reflective layer.

7. The process for producing a reflective mask blank for EUV lithography according to claim 4, wherein the pressure in the step of forming the absorber layer is at least $3.0 \times 10^{-2}$ [Pa] and at most $1.5 \times 10$ [Pa].

8. The process for producing a reflective mask blank for EUV lithography according to claim 4, wherein of the absorber layer, the light reflectivity at a wavelength of inspection light within a wavelength range of from 150 to 600 nm is at least 20%.

9. The process for producing a reflective mask blank for EUV lithography according to claim 4, wherein the angle of growth of defects on the absorber layer is at least 0 [deg].

10. The process for producing a reflective mask blank for EUV lithography according to claim 4, wherein the root mean square roughness Rq of the surface of the multilayer reflective film is at most 0.30 [nm], and the root mean square roughness Rq of the surface of the absorber layer is at most 0.50 [nm].

11. A reflective mask blank for EUV lithography having a multilayer reflective film for reflecting EUV light and an absorber layer for absorbing EUV light formed in this order on a substrate, wherein the ratio of the size of a local irregularity on the surface of the absorber layer resulting from an amplitude defect present in the vicinity of the surface of the multilayer reflective film, to the size of the amplitude defects, is at least 1 and at most 2.

12. A reflective mask blank for EUV lithography having a multilayer reflective film for reflecting EUV light and an absorber layer for absorbing EUV light formed in this order on a substrate, wherein the ratio of the size of a local irregularity on the surface of the absorber layer resulting from an amplitude defect present in the vicinity of the surface of the multilayer reflective film, to the size of the amplitude defects, is at least 1 and at most 1.5.

* * * * *